(12) United States Patent
Neushul

(10) Patent No.: US 8,378,327 B2
(45) Date of Patent: Feb. 19, 2013

(54) COMBINATION COMPUTED AND DIRECT RADIOGRAPHY SYSTEM AND METHOD

(75) Inventor: Stephen Neushul, Rancho Palos Verdes, CA (US)

(73) Assignee: iCRco, Inc., Torrance, CA (US)

( * ) Notice: Subject to any disclaimer, the term of this patent is extended or adjusted under 35 U.S.C. 154(b) by 0 days.

(21) Appl. No.: 13/304,621

(22) Filed: Nov. 26, 2011

(65) Prior Publication Data

US 2012/0187310 A1      Jul. 26, 2012

Related U.S. Application Data

(60) Provisional application No. 61/417,423, filed on Nov. 27, 2010.

(51) Int. Cl.
*G03B 42/08* (2006.01)
(52) U.S. Cl. ..................................... 250/585; 250/484.4
(58) Field of Classification Search ............... 250/484.4, 250/580, 581, 582, 583, 584, 585, 586, 589
See application file for complete search history.

(56) References Cited

U.S. PATENT DOCUMENTS

2010/0148096 A1 *   6/2010   Neushul ........................ 250/585

* cited by examiner

*Primary Examiner* — Mark R Gaworecki
(74) *Attorney, Agent, or Firm* — Rowlett Law Firm; Robert Rowlett

(57) ABSTRACT

A scanning apparatus that can operate as both a computed and direct style radiography device. In the computed radiography mode, an internal imaging plate is removed or maintained inwardly within the housing assembly to allow a cassette handling mechanism holding a removable imaging plate to pass adjacent the scanning head. In the direct radiography mode, the cassette handling mechanism is retracted and the internal imaging plate is moved outward from the within the housing such that it is located adjacent the reading slot of the scan head assembly. In both modes of operation, the imaging plate being used is maintained adjacent the scan head while the scan head and imaging plate surface are moved relative to each other allowing the scanning and acquisition of the image data stored on the plate.

15 Claims, 15 Drawing Sheets

COMBINATION COMPUTED AND DIRECT RADIOGRAPHY SYSTEM AND METHOD

CROSS REFERENCE TO RELATED APPLICATIONS

This application claims priority to and the benefit of U.S. Provisional Application No. 61/417,423 filed, Nov. 27, 2010, entitled, Combination Computed anti Direct Radiography System And Method.

BACKGROUND

1. Field of the Invention

The present invention relates generally to radiography systems and more specifically to a combination modular computed and direct radiography system and method.

2. Background of the Invention

Computed radiography ("CR") systems generate a digital image of an x-ray by scanning an x-ray storage phosphor imaging plate that has been exposed to x-ray energy, usually while at least partially housed in a cassette. The re-useable imaging plate replaces the need for previously conventional x-ray film. The imaging plate is typically coated with photo-stimulable storage phosphors allowing it to store the energy received from the x-ray irradiation. The cassette encases the imaging plate and prevent exposure from ambient and other light sources In a typical CR procedure, the desired object is exposed to x-rays from one perspective with the imaging plate generally positioned on the opposite side so as to capture those x-rays passing through the object. This results in a latent image being formed and stored on the imaging plate. Multiple plates may be used for multiple x-rays images of the desired object or person or for a larger x-ray image. After exposure by x-rays, the imaging plate is encased in its cassette and taken to a CR system for image processing.

The CR device creates an image by stimulating the storage phosphors within the imaging plate using a laser beam, typically with a wavelength from between 600 nm to 800 nm, driven across the irradiated area of the imaging plate. Point by point or line by line stimulation by the laser causes the imaging plate to release light in direct proportion to the latent energy previously stored as a result of the x-ray irradiation hitting the surface of the phosphors. The light released by the imaging plate is captured by the CR scanning and optical system and converted into an electrical signal. This signal is then converted to digital data that can be manipulated and ultimately viewed on a monitor, printed, transferred to remote systems for further analysis, storage or computations.

Various companies produce CR systems with each using slightly different means for exciting the phosphor plate and capturing the released light energy as well as handling the imaging plate. The advantages and drawbacks of these CR systems relative to other radiography systems are well known. Commonly cited drawbacks include the need to typically handle the imaging plate within a cassette, the burden of moving the imaging plate cassette from the x-ray exposure position to the CR system and then scanning it to obtain the desired image. In addition to requiring additional handling, these efforts increase the time before an image is actually created by the CR system. Other cited drawbacks include the overall size of the system, cost and complexity of the devices, including the time and costs associated with repairing and maintenance.

Direct radiography ("DR") systems are another form of x-ray imaging similar to CR systems in that they typically employ phosphor scintillation materials to generate an image. These systems, however, do not use cassettes containing imaging plates. In a typical DR system, the x-ray energy is directed through the desired object and onto a DR imaging plate assembly. The typical DR imaging plate utilizes phosphor scintillation material bonded to pixel sized sensors. X-ray energy hitting the phosphor layer generates energy that is sensed by each pixel sensor within the detector and sent directly to the DR system amplifications electronics for generation of the image or other data. In a DR system, no intermediate steps or processes are required to obtain the image data.

In addition to generally eliminating the burden and time required to move the imaging plate cassette from the x-ray position to the CR system, most DR systems also advantageously utilize a scaled imaging plate. Because the sealed plate does not need to maintain stored x-ray energy or be moved for processing, the risk of ambient light or other contaminants affecting the otherwise stored latent image is eliminated.

What is also needed is a single device that has the advantages of both CR and DR and that can be used in both applications.

SUMMARY

The present invention is directed to a modular radiology device that can be advantageously used in both computed radiology and fixed scanning direct radiology devices as well as in a combination device. The modular radiology system has an external housing and frame structure that supports a scanning assembly that is adapted to be used in both the CR mode of operation as well as the DR mode of operation. The scanning assembly includes an exterior housing adapted to be moved along the elongated frame within the exterior housing of the radiography device. An imaging plate cassette carriage assembly is also coupled to the frame assembly and adapted to move a imaging plate cassette loaded into the carriage assembly into the exterior housing of the radiology device wherein it can be scanned and the image date stored on the imaging plate acquired by the scanning assembly.

An optics assembly is secured within the scanning assembly housing and is adapted for generating and scanning a focused laser beam through a narrow elongated opening in the housing such that it can be directed over an imaging plate, surface or detector panel. The optics assembly includes a laser, a scanning assembly and a plurality of folding mirrors that are adapted to scan the laser beam and direct the scanning laser beam through the opening in the scanning assembly housing and over the imaging storage surface. The scanning assembly also includes a light collection and light measuring assembly secured within the housing. The light collection assembly includes a plurality of generally opposing curved reflective surfaces that are adapted to reflect light received through a reading slot in the scanning assembly housing and direct it to a light measuring device. The light measuring devices forward the light information to an electronics module for image processing.

The frame assembly supports a generally fixed imaging storage plate that is movable between a first position and a second position. In the first position, the fixed imaging plate is retracted away from the scanning path so as to allow sufficient room for the cassette carriage assembly to pass. In this mode of operation, the radiography device acts as a CR system as the scanning assembly acquires images from cassettes loaded into the cassette carriage assembly.

The fixed imaging plate may also be moved into a second position through a series of rotating members and linkages coupling the fixed imaging plate to the frame assembly and moving it relative to the scanning assembly. Prior to moving into the second position, the cassette carriage may be locked to prevent further loading of imaging plates. In the second position, the radiography device operates and functions as a DR system by utilizing the fixed imaging plate within the housing to store and then acquire images. In this mode of operation, the x-ray images are taken over the desired object or patient and the radiography device, which houses the fixed imaging plate. There is no need to remove the imaging plate from the carriage to take new images. In this second position, the fixed imaging plate is advantageously moved from the first retracted position within the exterior housing to the second position adjacent to the scanning assembly to allow proper scanning and image acquisition. In yet another embodiment, the imaging plate may be moved into either the first or second position from the cassette carriage assembly.

BRIEF DESCRIPTION OF THE DRAWINGS

Embodiments of the invention are illustrated by way of example and not by way of limitation in the figures of the accompanying drawings in which like references indicate similar elements. It should be noted that different references to "an" or "one" embodiment in this disclosure are not necessarily to the same embodiment, and such references mean at least one.

DETAILED DESCRIPTION OF THE INVENTION

Existing computed radiography ("CR") designs providing quality imaging characteristics and methods are complex and expensive to manufacture, maintain and repair. The problems of expense and complexity of manufacture, maintenance and repair are generally deemed worse when associated with existing direct radiography ("DR") designs. In addition, downtown costs associated with maintaining and servicing current CR and DR devices, can be critical with such existing designs.

In the present design and methods, novel modular components and assemblies are provided that find application in both CR and fixed imaging plate scanning devices, including DR applications. The novel design and application of these modular systems and components minimize or avoid altogether, the high costs and delays previously associated with repairs and maintenance. For example, the use of the presently designed modular systems generally eliminates the requirement that the radiology device be shipped back to the manufacturer or service facility for major service or repair or delays in getting qualified service technicians to the repair site.

More specifically, the present invention discloses a novel modular laser scanning and reading assembly that is adapted to work with novel drive and frame assemblies and a modular electronics assembly to create a modular built radiology device. The present invention further discloses a novel DR device that provides high resolution images and reliability of traditional CR devices but retains the compact and scaled imaging plate advantages of traditional DR devices.

Figure 1:
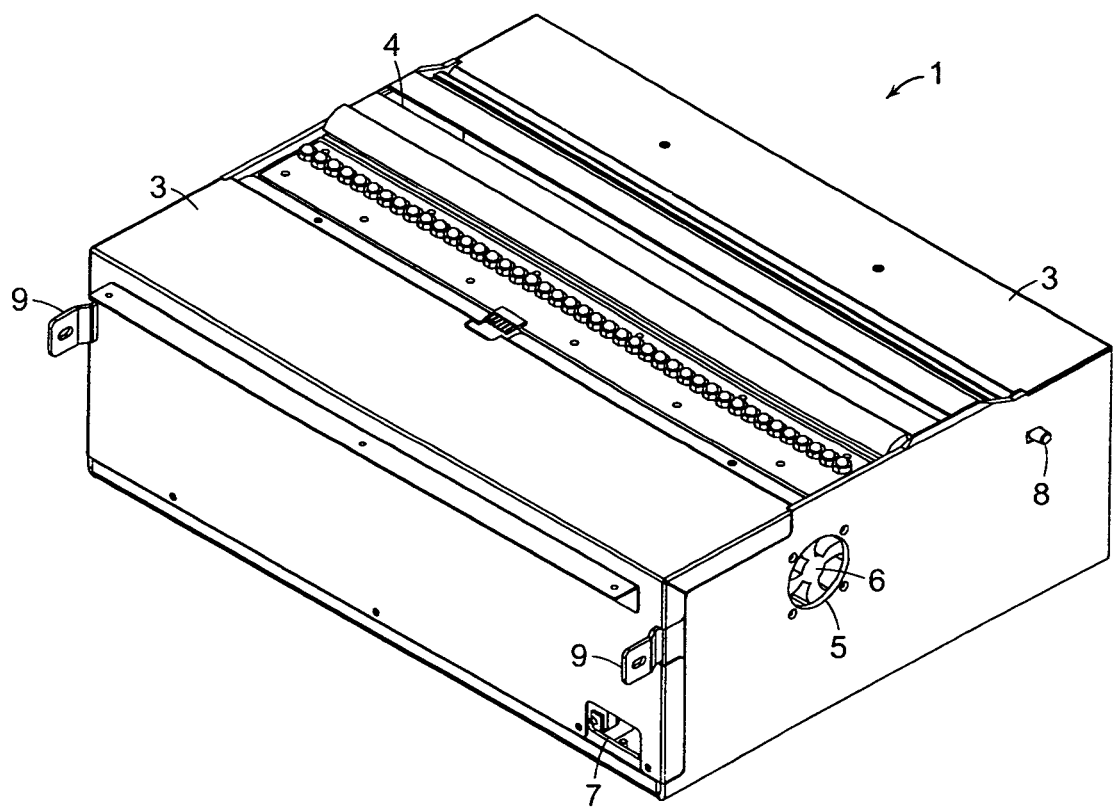
FIG. 1 shows a perspective view of an embodiment of the present invention.

Referring now to FIG. 1, the present invention provides a modular scanning assembly also referred to as a scan head assembly that is adapted for use with both CR and DR type devices. In the illustrated embodiment, the scanning assembly 1 includes an external housing 3 that is configured to maintain a generally light and dust tight internal environment and structurally support the internal optics. An elongated opening or slit 4 is provided on the underside of the housing 3 and adapted to allow for external scanning of the laser beam and also reading of image data from an imaging plate or plates as the scan head 1 scans over the imaging plate. The reading slit 4 may be covered with a light transparent material such as a glass to restrict the entry of dust or other contaminants or assist in focusing the laser beam.

The housing 3 preferably includes the ability to remove heat energy, including an air vent such as opening 5. To increase the removal of warm air, opening 5 is fitted with a fan 6. The fan 6 is used to move air and particularly, remove warm air from inside the housing 3 and maintain the internal optics and electronics at preferred operating temperature. The opening 5 is adapted to restrict light entry into housing 3 and is preferably fitted with a light restricting brush (not shown) or similar device that allows for air transfer while restricting exposing light entry. Alternatively, fan 6 may be used to draw in air, creating a positive pressure environment within the optical assembly and keeping out contaminants.

The housing 3 is also fitted with an electrical and data connection 7, including an electrical/data plug or receptacle for connection with an electronics module (not shown) external to scan head 1. The scanning assembly 1 requires electrical power for operation and trails means for transferring image data. Thus, electrical connection 7 may comprise a plurality of electrical and data connection points, including separate ports for power and for data transfer.

The housing 3 is also fitted with mounting means for securing the scanning assembly 1 into the desired digital radiology device. In the embodiment shown, the housing 3 is fitted with a pair of mounting pins 8 that protrude outwardly from opposing side walls. Pins 8 are adapted to fit into mating slots provided within the desired radiology device. These slots or grooves may include a desired path to assist in the installation and removal of the scan head 1. Pins 8 may be made from small diameter rod that is bolted, welded or otherwise secured to the side wall of housing 3. Alternatively, or in addition, scanning assembly 1 may be provided with mounting clips or brackets 9. The use of brackets 9 allows the scanning assembly 1 to be secured within the desired radiology device through the use of fasteners that secure to the radiology device.

During installation, pins 8 are inserted into matching slots fitted within the frame or housing of a desired radiology device. With the pins 8 positioned within their mating slots, scan head 1 may then be rotated or positioned into the radiology device and preferably, between the frame members. Once positioned, the scanning assembly 1 may be secured to the frame or radiology device housing using fasteners fitted through brackets 9. To remove the scanning assembly 1, the fasteners are removed from the brackets 9 and the scan head is simply rotated and pulled until the pins 8 are withdrawn from the matching slots within the radiology device. To fully remove the scan head 1, all electrical and data connections (not shown) would also be removed.

By providing radiology devices having matching mounting means, the scanning assembly 1 advantageously provides a modular optical and scanning system that can be readily installed or removed from any such configured device. Most any method of securing the scanning assembly 1 within the desired radiology device may be used. The presently described embodiment only requires two fasteners through mounting brackets 9 and along with pins 8 and matching slots in the frame members, substantially reduces the chance of a failed or incorrect installation. This simple installation and removal procedure eliminates the need for specialized service technicians for servicing because the entire scanning assembly 1 can now simply be replaced with a replacement unit as opposed to servicing or repair.

Figure 2:
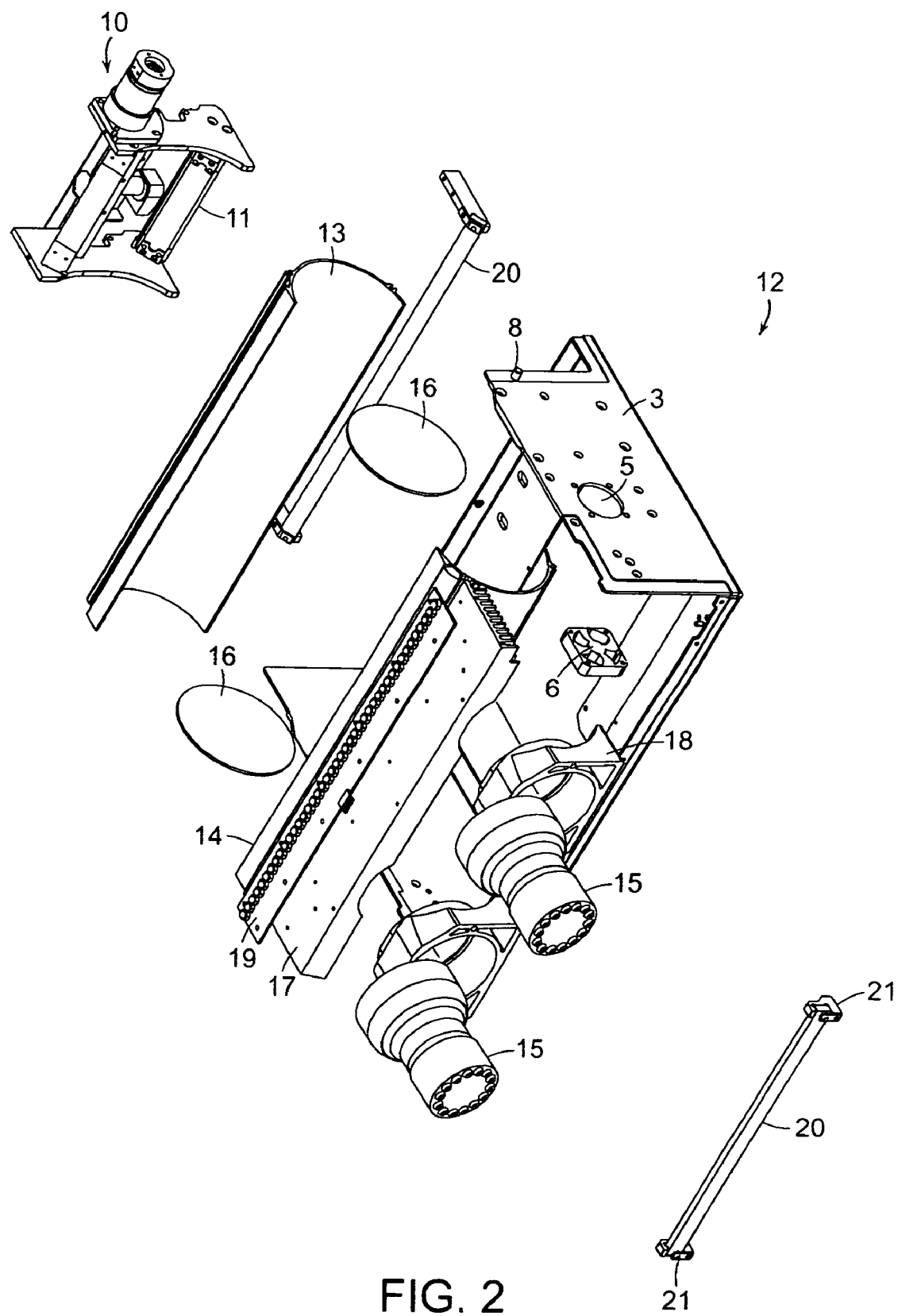
FIG. 2 shows an exploded partial assembly view of an embodiment the present invention.
Figure 3A:
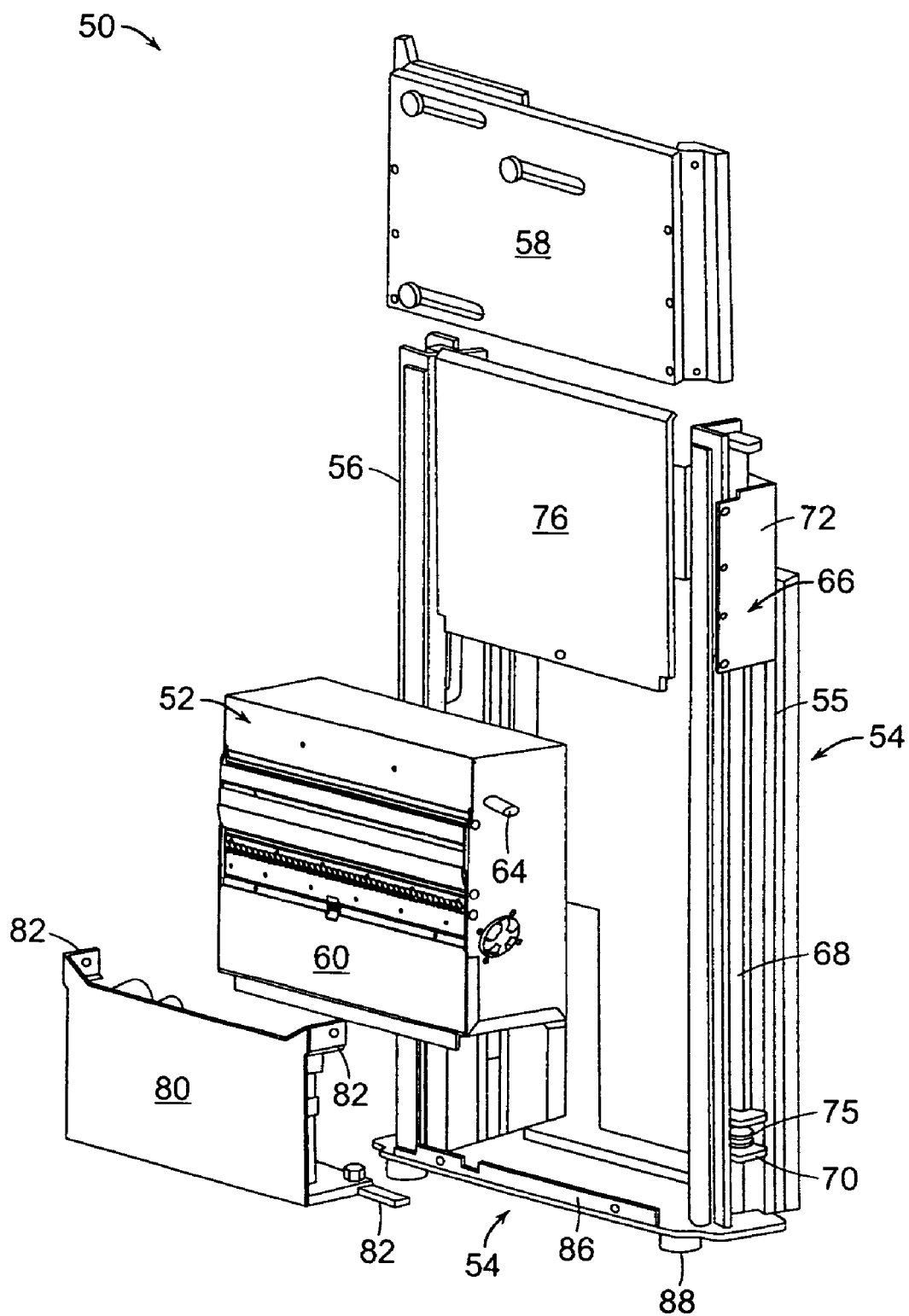
FIG. 3A shows a perspective partial disassembled view of an embodiment of CR system of the present invention with the covers removed.
Figure 3B:
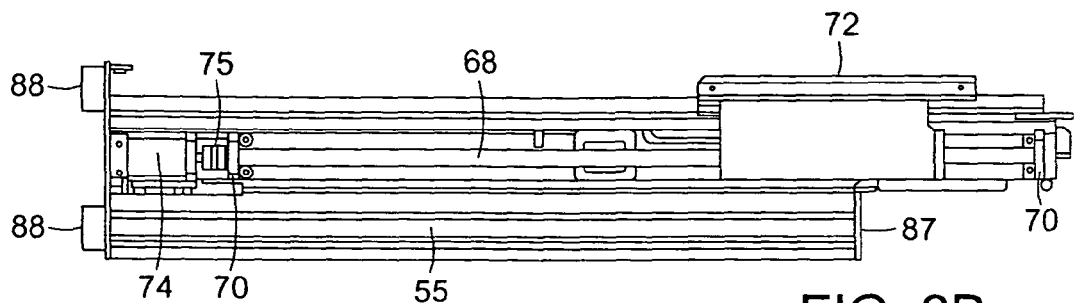
FIG. 3B shows a side view of an embodiment of a partially disassembled frame assembly of the CR system of the present invention.
Figure 3C:
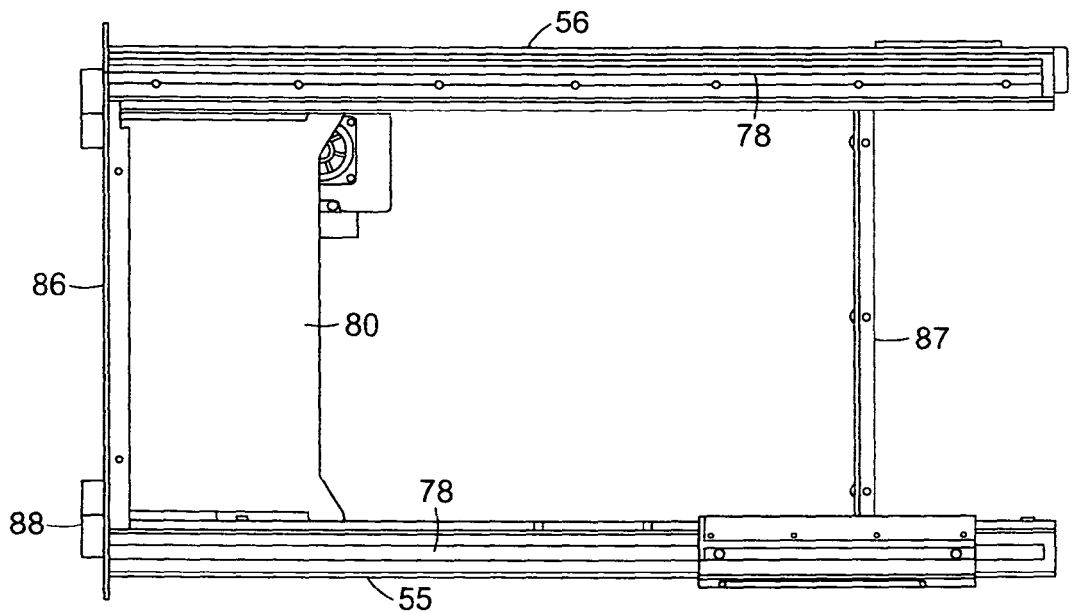
FIG. 3C shows a front view of an embodiment of the frame assembly of the CR system of the present invention.
Figure 3D:
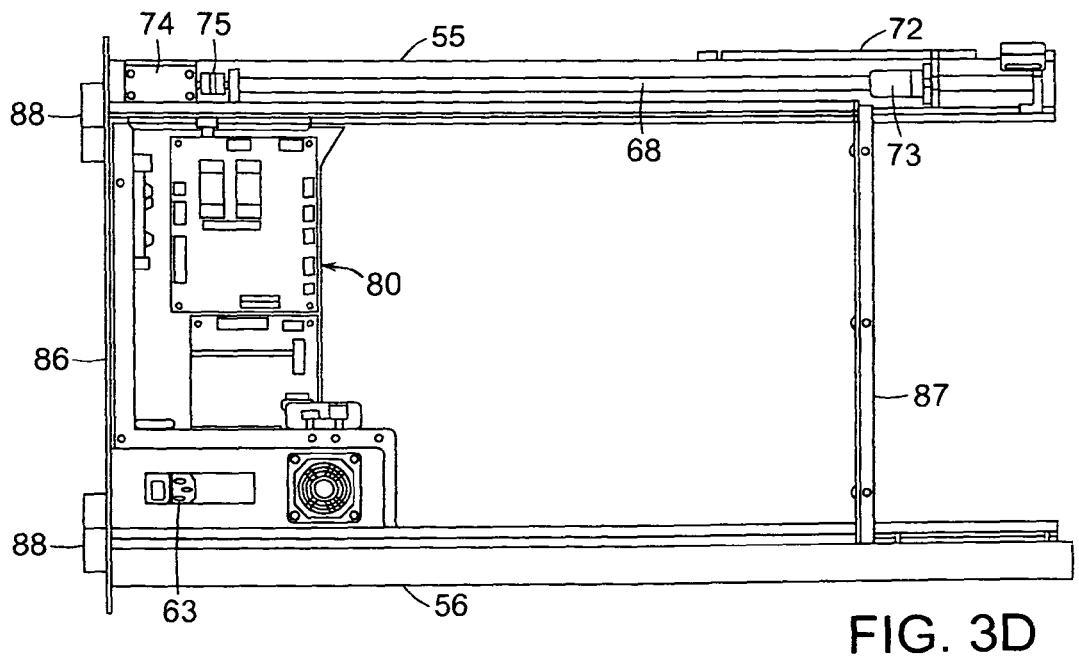
FIG. 3D shows a rear view of an embodiment of a partially disassembled frame assembly of the CR system of the present invention.

Referring now to FIG. 2 in conjunction with FIG. 1, an exploded view of the scanning assembly 1 is shown and particularly of the novel and compact optical assembly contained within housing 3. A laser assembly 10, includes a laser, galvo and attached rotating mirror assembly secured together using a novel bracket that preferably also supports folding mirror 11. Laser assembly 10, in conjunction with a unique focusing mirror arrangement, is adapted for scanning the laser beam through the narrow elongated opening 4 oriented along one side of housing 3. The supporting "H" style bracket of the laser assembly 10 is preferably secured within housing 3 using vibration dampening mounts and methods as are well known.

A light collection assembly 12 is also mounted within the housing 3. The light collection assembly 12 includes a plurality of opposing reflecting surfaces 13 and 14 adapted to reflect light received from the scanned imaging plate (not shown) onto a pair of light measuring and amplification devices 15. Preferably, the light measuring and amplification devices 15 are photomultiplier tubes but may also comprise CCD sensors, CMOS sensors, silicone diode sensors or similar light measuring devices coupled with necessary amplification electronics. The light collection assembly 12 is specifically adapted to receive and measure light from an imaging plate as it is scanned by a focused laser beam from laser assembly 10.

Reflecting surfaces 13 and 14 are preferably opposing interior cylindrical surfaces with an end cap 16 secured and covering each end. End caps 16 are advantageously designed to maintain proper spacing between reflective surfaces and aid in reflecting light to light measuring sensors 15. All reflective surfaces are adapted to enhance reflectivity and may be polished. Preferably, reflective surfaces 13 and 14 and end caps 16 are covered with a highly reflective coating or surface layer to ensure the maximum amount of light received from the scanned imaging plate is directed to the photo multiplier tubes 15. Any highly reflective coating, polishing or reflective surface material and method could be used, including a layer or coating of a synthetic fluoropolymer. In one embodiment, a layer of expanded polytetrafluoroethylene such as one available from WL Gore & Associates, Inc. is used on reflective surfaces. The reflective material is cut to shape and adhered to and covers the reflective portions of cylindrical surfaces 13 and 14 and end caps 16. Alternatively such reflective material may also be spray applied, hot melt applied or applied as specified by the manufacture of the desired reflective material. Reflective coatings and surfaces may and may also be used on all reflective surfaces within the scanning assembly 1. Similarly, all non reflective surfaces within the scanning assembly 1 may be covered with or coated with a non-reflective material to reduce unwanted light reflection.

In one embodiment, reflective surfaces 14 and 15 are one piece integral components, including surfaces adapted for mounting and securing other components and are made from an extruded material such as an extruded aluminum. At least one of the reflective surfaces 14 may include a heat sink 17 for removing heat. Heat sink 17 advantageously removes heat, enabling the use of an integral eraser assembly within the scanning assembly 1. To reduce costs and complexity and increase heat transfer, heat sink 17 or heat sinks are extruded as part of reflective surface extrusion 14. In the present embodiment, reflective surface 14 and heat sink 17 form an integral aluminum extrusion that is adapted to secure an integral erasure assembly 19. The reflective surface 14 and heat sink 17 extrusion is further adapted to remove sufficient heat allowing the erasure assembly 19 to operate concurrently during the scanning operation.

Erasure assembly 19 comprises a light generating assembly adapted to illuminate the imaging plate after scanning to remove the latent image and ready the plate for further x-ray exposure. Preferably, the erasure assembly 19 comprises a plurality of light elements such as LEDs that are mounted on a strip and secured to the heat sink 17 so as to ensure heat transfer from the erasure tights to the heat sink. A heat transfer interface may be used between the heat sink 17 and erasure 19 to facilitate such heat transfer. In an alternative embodiment, a plurality of erasure assemblies may be used and each may be secured to a heat sink. Additional heat sinks 17 may be extruded as part of either reflective surface components 13 and 14 or both, or may be secured thereto, as needed for each particular digital radiography application. Preferably, erasure assembly 19 is spaced apart from scanning and reading slot 4 and separated using a light blocking device such as a caterpillar brush.

In the optical assembly of the present scanning assembly 1, folding mirrors are advantageously used to reduce the otherwise necessary focal length required to ensure the laser beam from laser assembly 10 remains focused as it scans across the entire width of an imaging plate. Specifically, to ensure high quality reading of the data stored on imaging plates, it is imperative the scanning laser beam remain focused as it scans across the width of the plate. Typically, a focal distance of over twenty inches is necessary to maintain a focused laser beam on a conventional plate of width not exceeding 14 inches.

The present invention advantageously maintains the relative focal length of conventional systems while reducing the actual physical length necessary for such focus. By using a folding mirror arrangement 20 and 11 in conjunction with the laser assembly 10 and a reading slot 4 oriented perpendicular to the imaging plate, the scanning assembly 1 maintains a focused laser beam across scan widths even greater than that of conventional imaging plates while advantageously reducing the size of the optical assembly 12 and thus scanning assembly 1. The present optical system 12 uses a plurality of front surface reflectivity mirrors as folding mirrors to maintain the desired relative local distance. In the presently disclosed embodiment, at least one of the folding mirrors 20 may be adjustably mounted within the housing 3 to allow for fine focus adjustment of the laser beam. In this embodiment, adjustable mounting bases 21 secure each end of the elongated return folding mirror 20. Rotating adjustment screws within the mounting bases 21 acts to advantageously adjust the folding mirror 20 along two dimensions.

The embodiment shown utilizes three front surface reflectivity mirrors 20 and 11 to fold light in the corners. At least one of the mirrors 20 is generally the width of the widest desired imaging plate with another mirror 11 being much narrower and secured to the "H" styled bracket of the laser assembly 10. The novel design of the present scanning assembly 1 provides for scaleability such that the laser beam ay be maintained in focus across a wider scan width through minor adjustments to the laser assembly 10 and folding mirror arrangement 20 & 11 and only requiring correspondingly wider folding mirrors and scanning assembly.

Computed Radiography Application.

Referring now to FIGS. 3A-3D, a specific embodiment of the present invention enables an age reading device 50 utilizing an embodiment of the scanning assembly of the present invention 52 within a novel elongated frame assembly 54. The modular scanning assembly 52 is adapted to mount within the frame assembly 52 in a plug and play fashion to facilitate the assembly, maintenance, repair and disassembly of the imaging device 50. In the embodiment shown, the modular scanning assembly 52 is secured to the frame assembly 54 between the generally parallel elongated frame members 55 and 56 using a four point connection means.

The computed radiology ("CR") imaging device 50 includes a cassette carriage module 58 for supporting an imaging plate cassette assembly such as the one described in U.S. Pat. No. 7,375,350 to Stephen Neushul. The carriage module 58 may also be adapted to support an imaging cassette and plate of most any size that can be driven within the frame assembly 54 such that the desired portion of the imaging plate (not shown) is driven past the scan head 52.

A drive assembly 66 is secured to one side of the frame assembly 54 along frame member 55 and also coupled to the moveable carriage assembly 58. The drive assembly 66 is adapted to move the carriage 58 and any inserted imaging plate cassette from a first position at one end of the frame assembly 54 generally parallel with the elongated frame members 55 and 56 to a second position nearer the opposite end of the frame assembly such that the carriage assembly is driven over the scanning assembly 52 such that the imaging plate can be scanned. A carriage support plate 76 is coupled to the moving portion of the drive assembly 66 at one side and slideably coupled along an elongated rail 78 (FIG. 5) on the other side that extends along the length of frame member 56. The carriage 58 may also be supported by a second elongated bearing type rail support positioned parallel to and generally adjacent the drive assembly 66. The rails 78 may be supported and attached to frame members 55 and 56 through rail supporting members or directly attached with post supports, fasteners, welding, or any other method as is well known.

An electronics module 80 is secured between frame members 55 and 56. The electronics module includes electrical couplers adapted to connect directly to the scan head module 52. In the embodiment shown, the electronics module 80 is secured within the frame assembly 54 between frame members 55 and 56 using a plurality of screws secured through brackets 82 on the frame module extending into the frame members. The electronics module, like the other modules and components of the present invention, may also be secured to the frame assembly 54 using other fastener types and securing means as are well known in the art.

A frame end cap 86 secures the side frame members 55 and 56 at one end and advantageously acts to provide closure for the end of the CR device 50. In the embodiment shown, the end cap 86 acts as a base for the CR 50 and supports feet 88 adapted to prevent movement on the supporting surface and also to reduce vibration. Base supports 88 may be a rubber base that is secured to end cap 86 or alternatively any type of base or footing material may be used, such as the four pliable feet screwed into the end cap as shown in the Figure. An upper lateral frame member 89 extends laterally between frame members 55 and 56 and adds structural rigidity to the frame assembly 54 and further provides mounting locations for an exterior enclosure. Although the frame members 55, 56 and 87 and end cap 86 in the present embodiment are secured together using machine screws, they may also be secured using any other common means of fastening, including welding or even build from formed pieces.

Figure 4:
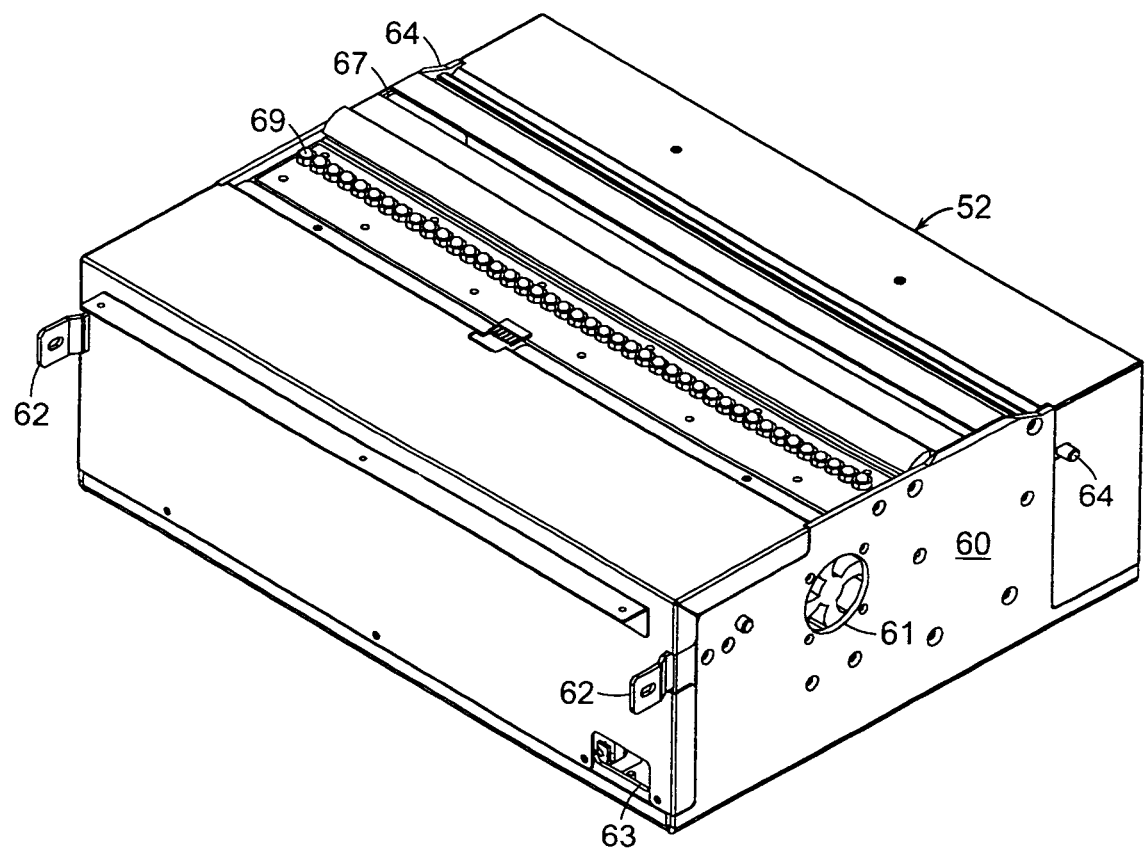
FIG. 4 shows a perspective view of an embodiment of the scanning assembly adapted for use in the CR device of the present invention.

Referring now to FIG. 4, the modular scanning assembly 52 includes a housing 60 that is adapted for removable attachment to the frame assembly 54 to facilitate its installation, servicing and removal. The housing 60 includes an exhaust vent 61 that preferably incorporate a cooling fan and brush system to vent warm air without allowing ambient light penetration and electrical connectors 63 for electrical and data connection with the electronics module 80. Scanning slot 67 provides an opening within the housing 60 for the laser beam scanning and receiving the emitted light for measuring and reading the image. Erasure assembly 69 is secured to housing 60 and is adapted for removing any latent image on the imaging plate.

Brackets 62 extend from the scan head housing 62. Each bracket 62 is adapted to accept a fastener for securing the scan head 52 to the frame assembly 54. The brackets 62 show have holes for a fastener (not shown) to pass through and secure the scan head 52 to the respective frame members 55 and 56. Alternatively, the brackets 62 may be adapted to directly connect to a fastener, pin, clip, hook or other coupler fixed to the frame assembly 54 or the brackets may extend from the frame assembly 54. The brackets 62 may be constructed as part of the scan head housing 60 or secured to it using one of the many well known techniques such as fastening, riveting, welding, adhesion or a combination.

In addition to brackets 62, the housing is also fitted with pins 64 located on opposite sides of the scan head housing 60. Each pin 64 is advantageously designed to mount into a slot 65 (FIG. 5) fitted to each frame member 55 and 56. The slot 65 is advantageously designed to allow for simply inserting and exact positioning of the scan head within the CR device 1. Thus, in the embodiment shown, the scan head module 52 is installed and removed using a four point attachment means and through the use of only two fasteners that secure it to the frame assembly 54.

Figure 5:
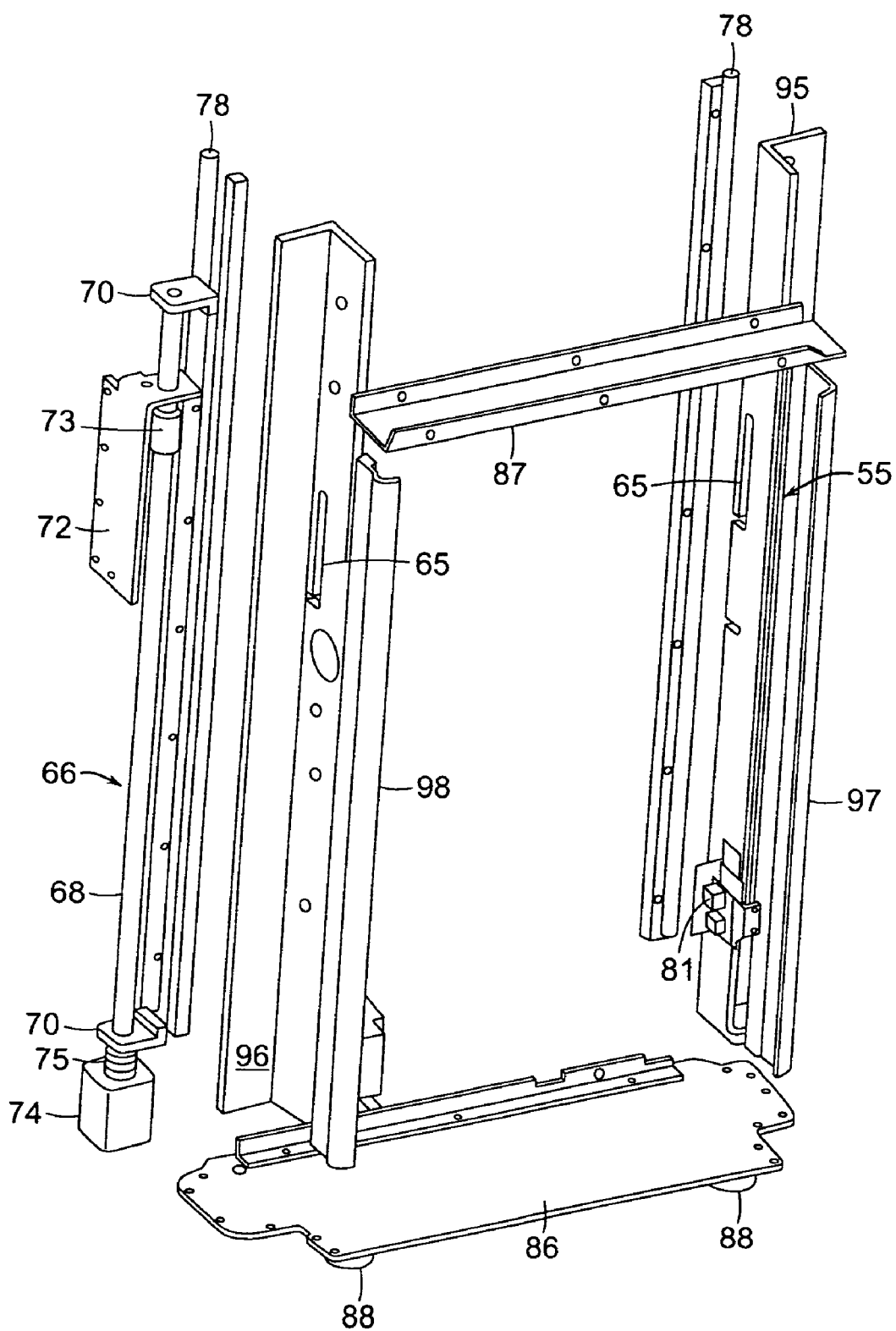
FIG. 5 shows an exploded view of an embodiment of the frame assembly of the CR system of the present invention.

Referring now to FIG. 5 in conjunction with FIGS. 3A through 3D, the drive assembly 66 includes a drive means 68, such as an acme type screw, a rack and pinion drive, a belt or chain drive, or similar drive mechanism that moves a drive plate 72 as it rotates or is otherwise driven. Spaced apart bearings 70 rotatably support the drive screw 68 and also secure the drive assembly 66 to the frame member 56. An electric motor 74 is attached to the drive screw 68 through coupler 75 and acts to rotate it. Preferably bearings 70 or similar rotation supporting devices are located adjacent the ends of the drive screw 68 and as illustrated, secured to the frame member 56 using vibration reducing mounts and machine screws to ensure rigid vibration free support while allowing maximum drive plate 72 travel. For longer travels that necessitate additional drive axle support, additional support bearings may be used that are slideably attached to an elongated bearing or bushing support rail that is in turn secured to the frame assembly 54.

The drive plate 72 is secured to the drive screw 68 through a drive block 73 that is driven along the drive screw 68 as it rotated by the electric motor 74. The drive assembly 66 is designed to be modular so as to facilitate installation, maintenance, repair and removal and well as to provide a very accurate and smooth drive mechanism. The drive assembly 66 could also be made using other means that accomplish accurate and smooth movement of the carriage assembly 58 along the length of the elongated frame members 55 and 56. For example, the presently described drive assembly 66 may be replaced with a linear motor assembly, a belt drive assembly a rack and pinion drive or any other drive means as commonly known in the art.

Figure 6:
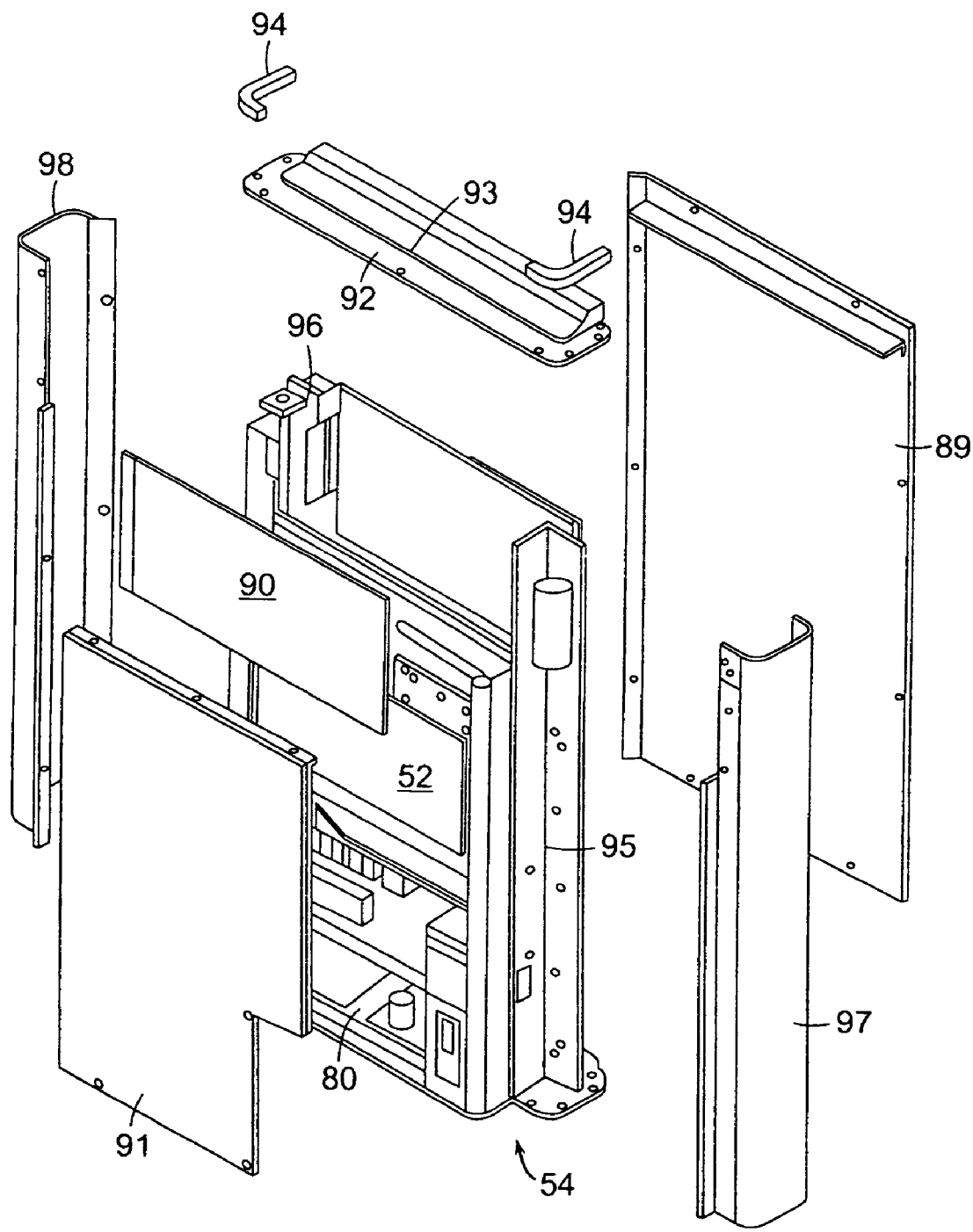
FIG. 6 shows a partial exploded view of an embodiment of the frame assembly and the covers of the CR system of the present invention.

Referring now to FIG. 6, an embodiment of the CR device 50 is shown with the drive module 66, electronics module 80 and scan head modules 52 installed within the partially disassembled frame assembly 54. To ensure the CR device 50 is light and dust tight, a back cover 89, upper front cover 90 and lower front cover 91, as well as top cover 92 are secured to the frame members 55 and 56. In one embodiment, covers, 89, 90, 91 and 92, are constructed from formed sheet metal, such as aluminum but may also be made from most any other durable material, including plastics and composites. The covers 89, 90 and 91 may be attached to the frame assembly 54 using machine screws or any other well known method, including, but not limited to, welding, snap fit, adhesives, formed covers that fit into slots, rivets, etc. The lower cover 91 is advantageously designed for removability and access to the scan head 52 and electronics module 80.

Upper cover 92 includes and opening slot 93 for receiving an imaging plate and particularly and imaging plate cassette. The opening slot 93 includes means for restricting the entry of ambient light when the imaging cassette is inserted as well as when it is removed. These means for restricting outside light may include a light restricting brush or brushes placed along the length of the slot, gaskets, as well as other means as commonly used in the art.

The frame assembly 54 is advantageously designed to form an exoskeleton that is sufficiently robust for a mobile type CR unit and rigid enough to support the precision drive module 66 and maintain the aligned cassette drive path. The exoskeletal frame assembly 54 comprises a plurality of elongated side members that fit together and mate to form the generally opposing side frame members 55 and 56 which are secured to upper lateral frame member 87 and lower end cap 86. Although the lower frame end cap 86 and lateral frame member 87 are designed as separate members that are secured to the elongated frame members 55 and 56 using screw fasteners, they may also be welded, joined through a mechanical tongue and slot fitting without or with less fasteners, secured using any form of fasteners, welded together, or even formed as part of the elongated side frame members.

In the embodiment shown, the frame members 55 and 56 each comprise a pair of extruded aluminum members that are joined along mating elongated edges to form a lightweight combination outer side wall and frame member. Specifically, frame member 55 is made from an angle extrusion 95 joined along an elongated side with a side extrusion 97. Similarly, side frame member 56 is made from an elongated angle extrusion 96 joined along an elongated edge with an elongated side extrusion 98. Each angle extrusion 95 and 96 is formed and adapted to geometrically mate, in a tongue and groove fashion, with the corresponding side frame member 97 and 98 along the mating elongated sides. The tongue and groove preferably extends along the length of the joined edges to increase rigidity, eliminate the need for fasteners and also prevent light intrusion. Joining each angled frame member 95 and 96 with respective side frame members 97 and 98 is readily accomplished by placing an extended tongue or lip that extends along the elongated side of the angled extrusion into a mating receiving groove or slot formed within the respective side frame member and rotating until the lip locks into the groove. Although the frame members could be secured using fasteners, adhesives or even welded together, the extruded tongue and groove creates a rigid assembly without the need or expense of such assemblies.

By using extrusions 95 and 97 and 96 and 98 that are paired together in a tongue and slot fashion and are further uniquely formed for the specific CR device application along with lateral frame members, the present embodiment provides a rigid chassis assembly 54 capable of supporting the required device modules 52 and 80 and drive system 66. In this embodiment, the drive system 66 is supported and secured between the angled frame member 96 and the side frame member 98. In addition, the angled extrusions 95 and 96 are each advantageously formed with securing means for the scanning assembly 52, including slots 65 for receiving pins 64 and brackets 62 along with supporting surfaces for mounting rails 78 and for supporting the exterior covers of the CR device 50 such as lower front cover 91.

Direct Radiography Application

Figure 7:
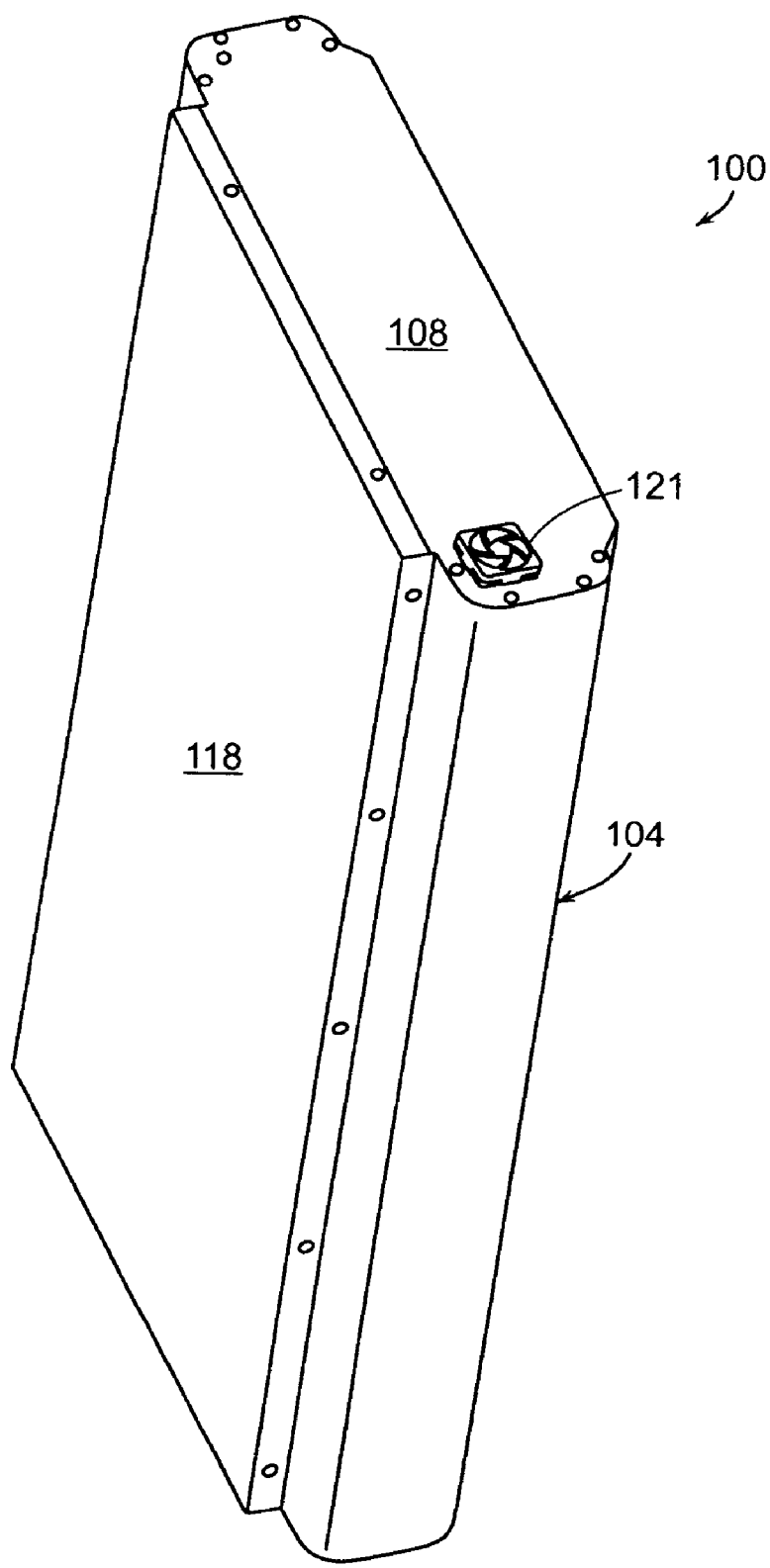
FIG. 7 shows an embodiment of the DR system of the present invention

Referring now to FIG. 7, another specific embodiment of the present invention enables a direct radiography type ("DR") image reading device 100 utilizing an embodiment of the inventive scanning assembly. Similar to the CR device embodiment, the present modular scanning assembly readily mounts within a rigid frame assembly 104 to facilitate the assembly, maintenance, repair and disassembly of the DR type imaging device 100. In contrast to the CR device 50 of FIGS. 3A through 6, however, the present DR embodiments function by moving the scanning assembly along the elongated length of the DR device and over an imaging plate that is generally fixed in position and secured to the frame.

Figure 8:
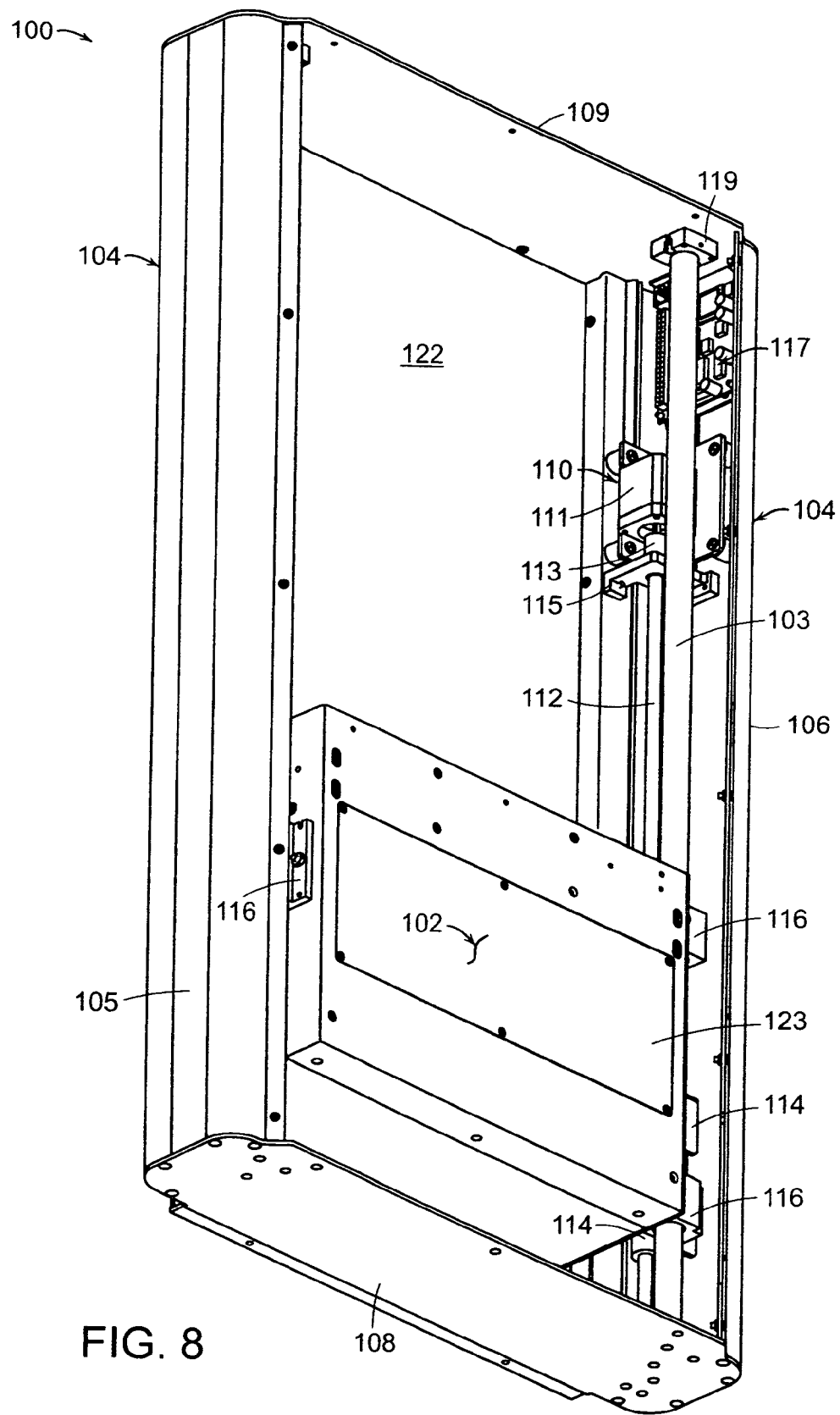
FIG. 8 shows a perspective view of an embodiment the DR system of the present invention with the outer top cover removed.
Figure 9:
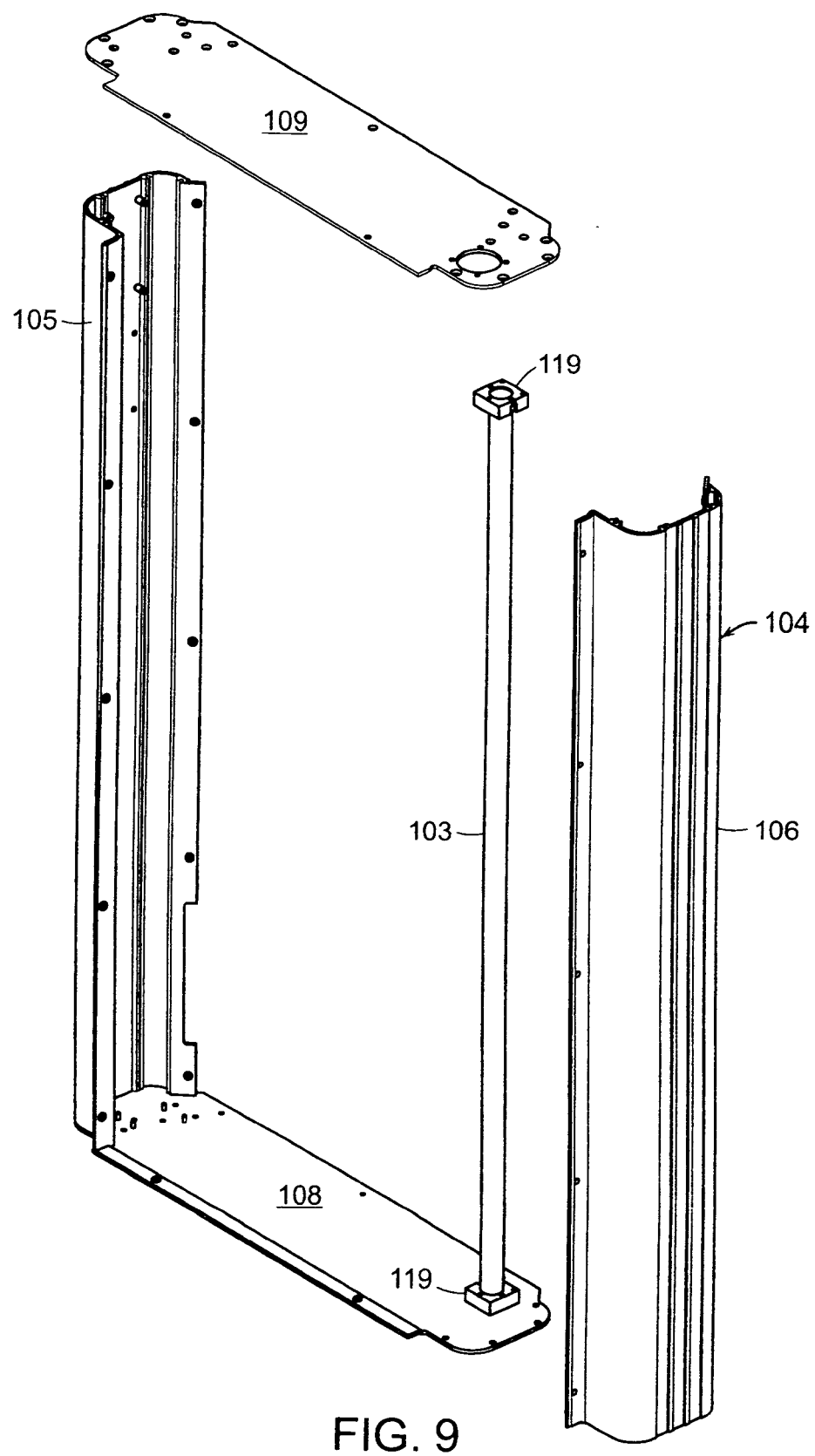
FIG. 9 shows an exploded view of the frame assembly of the D system of the present invention showing a rail for supporting a scanning assembly.

Referring now to FIGS. 8 and 9, the frame assembly 104 of the DR device 100 comprises a pair of generally opposing elongated side frame members 105 and 106 and generally opposing lateral side members 108 and 109. The frame assembly 104 is advantageously designed to form an exoskeleton that is sufficiently robust for a mobile type DR unit and rigid enough to support a precision drive system 110 and operation. The frame assembly 104 is further adapted to receive and support a scanning assembly 102. Similar to the CR system embodiment of the present invention, the elongated frame members 105 and 106 are preferably made from an extruded aluminum or other extruded metal. Opposing lateral frame members 108 and 109 are also preferably made from an extruded metal but may also be made from a plastic.

Drive assembly 110 is modular and similar to the disclosed drive assembly 66 utilized in the CR device 50 of FIG. 3 and includes a drive motor 111 coupled to a drive mechanism 112 through a shaft coupling 113. The drive mechanism 112 may be a drive screw, such as an acme type screw, that moves a mating internally threaded drive block 114 along its elongated axis as it is rotated by motor 111. In one embodiment, the drive motor is an electric motor with spaced apart bearings 115 rotatably supporting the acme type drive screw 112. The hearings 115 are preferably secured within a mount that secures the drive assembly 110 to the frame member 106 through a plurality of vibration mounts and fasteners.

For imaging devices, including the DR device 100, having longer travels, additional support bearings 115 may be used to ensure a precision drive path is maintained. Alternatively, support hearings may be used that slide along an elongated bearing or hushing support rail that is in turn secured to the frame assembly 106 as well as increased drive assembly 110 components, including the drive screw 112. Alternatively and as preciously discussed, different drive assembly may be used altogether so long as it maintains the necessary precision drive characteristics.

A drive block and bracket 114 is secured to the scan head module 102. The drive block 114 mates with the drive screw 112 such that when motor 111 is rotated, the scanning assembly 102 is moved along rails 103 that are secured to each frame member 105 and 106. A plurality of side rail bearings 116 slideably couple the scanning assembly 102 to elongated rails 103. In the embodiment shown, multiple spaced apart bearings 116 are secured to one side of the scanning assembly 102 and the adjacent side rail 103 and a single bearing is coupled to the other side of the scanning assembly and coupled to the respective side rail. This design advantageously resists torque from transferring from the drive assembly 110 to the scan head 102 during operation. Rails 103 may be made from smooth elongated rods or cylinders and preferably from a non-corroding or static producing material such as a stainless steel or one having a plastic surface or coating.

Similar to the disclosed CR embodiments, the DR device 100 includes an electrical interface 117 that is secured to one of the frame members 104 or 106 and is adapted for connection to a source of electrical power, such as a wall or other electrical outlet or battery supply. The electrical interface 117 is preferably also adapted to electronically connect with any desired receiver of image information, such as a computer, network, printer or the like though such connection may also be made using wireless methods as known in the art or transmitting information wirelessly. Electrical interface 117 is also adapted to electronically interconnect with the internal components, including the scanning assembly 102, the drive assembly 110 and the electronics module. Preferably all internal interconnects are with plug type wiring harnesses but may be interconnected using other means as is also well known. The electrical interface 117 may also be provided using multiple points of interconnection so as to facilitate wiring and the module assembly of device 100.

Figure 10:
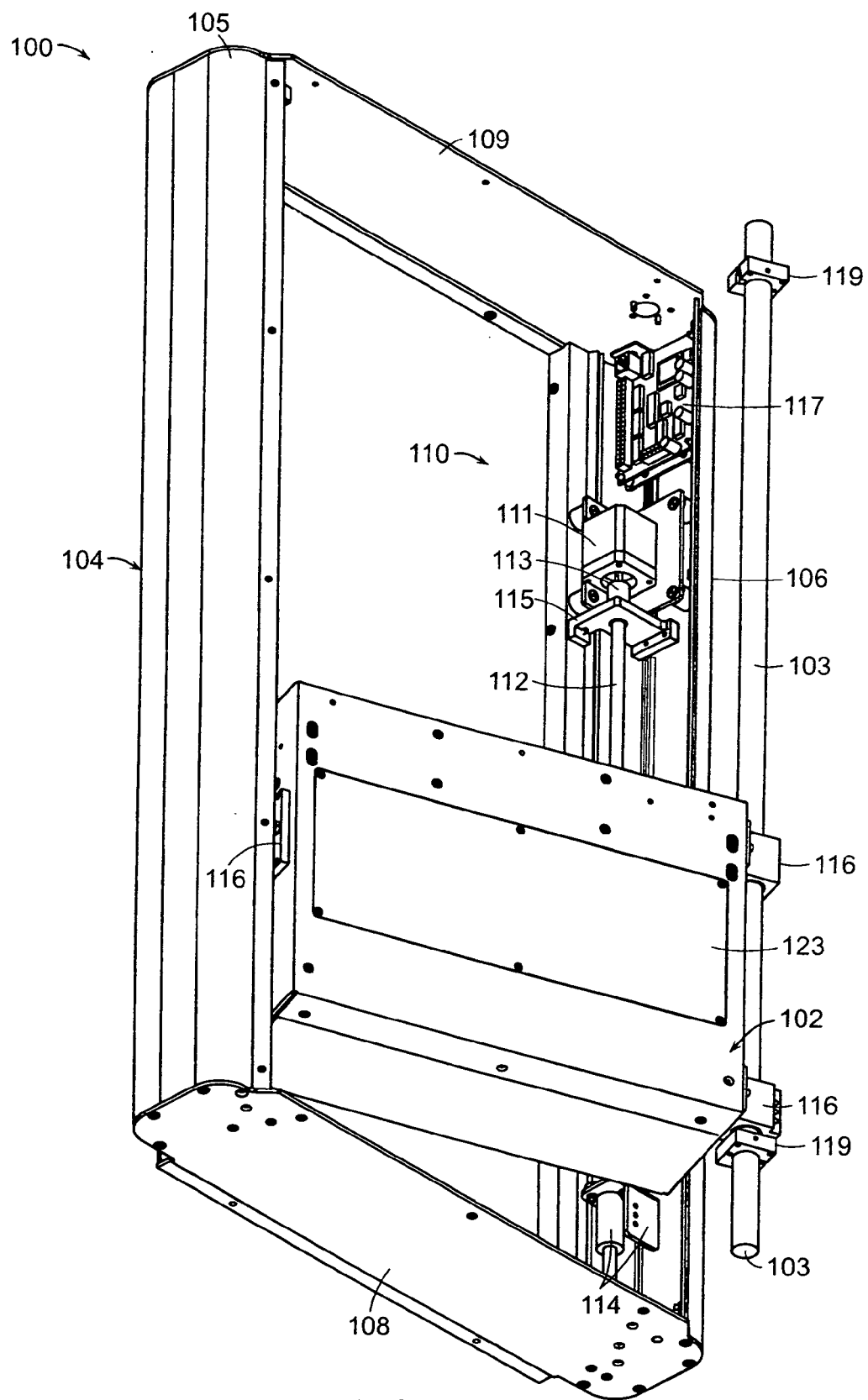
FIG. 10 shows a perspective view of an embodiment of the DR system of the present invention with the scanning assembly and support rail being installed into the frame.
Figure 11:
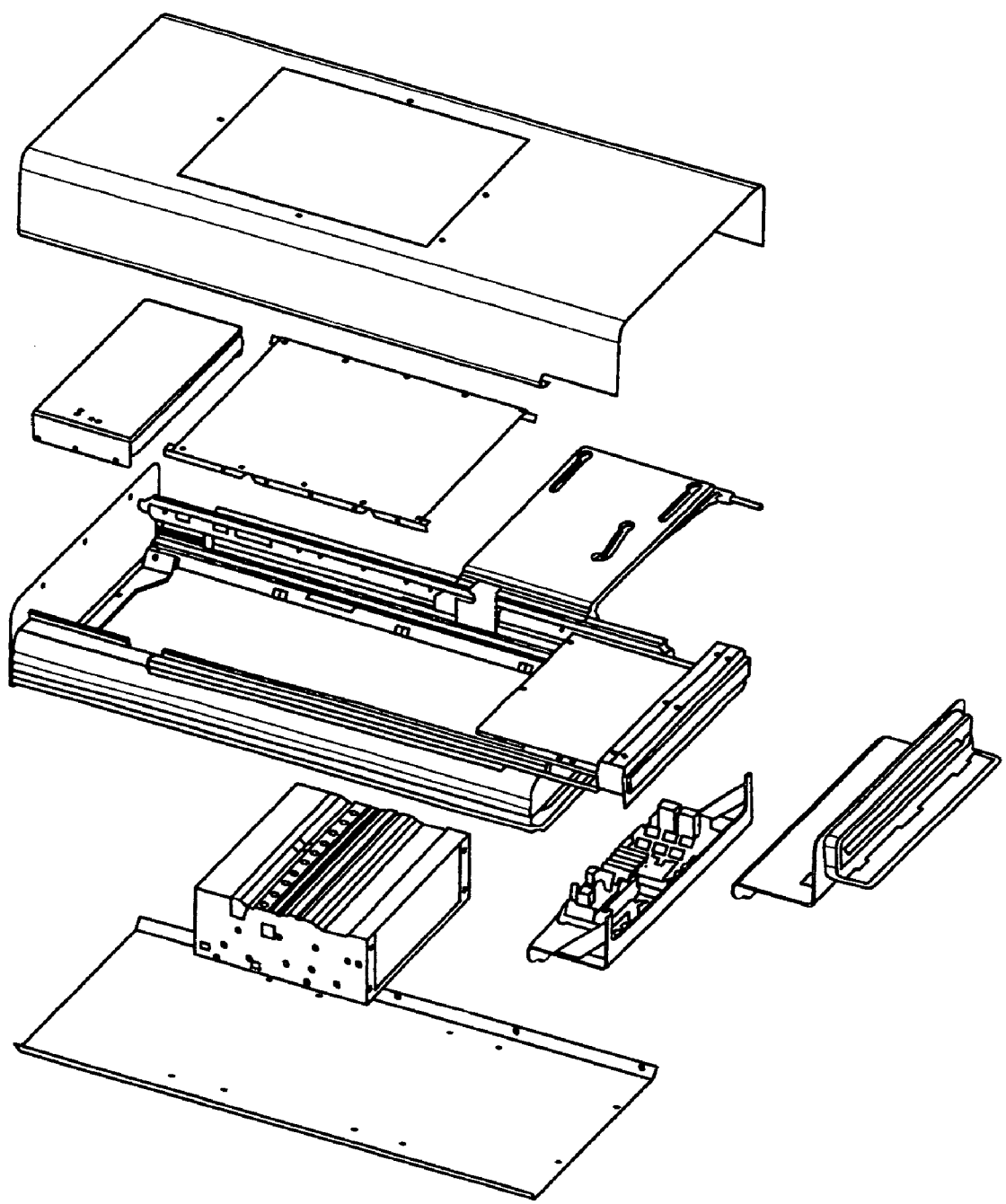
FIG. 11 shows an exploded view of the combination CR DR apparatus of the present invention.
Figure 12:
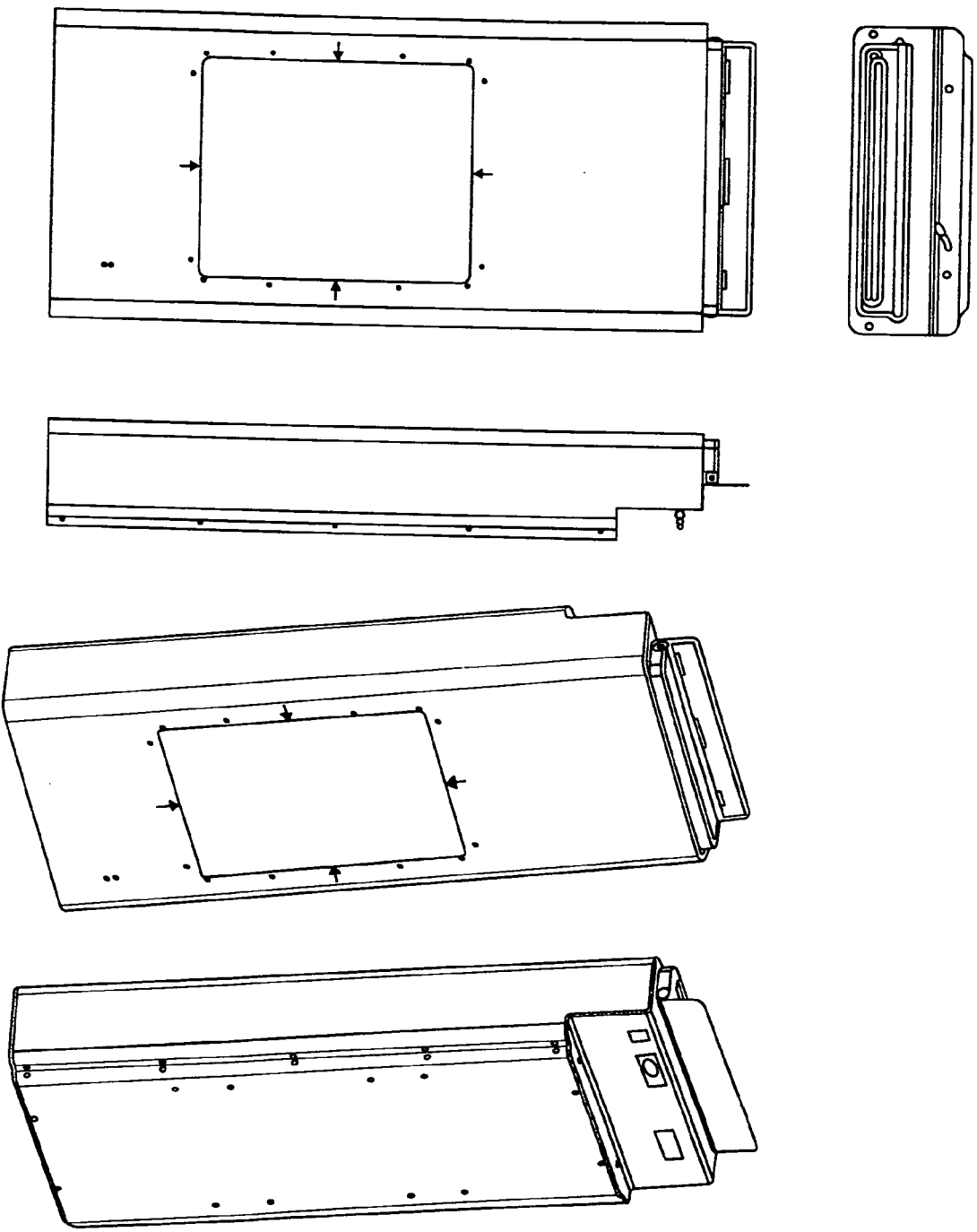
FIG. 12 shows a top, front, side and multiple perspective views of an embodiment of the combination CR DR apparatus of the present invention.
Figure 13:
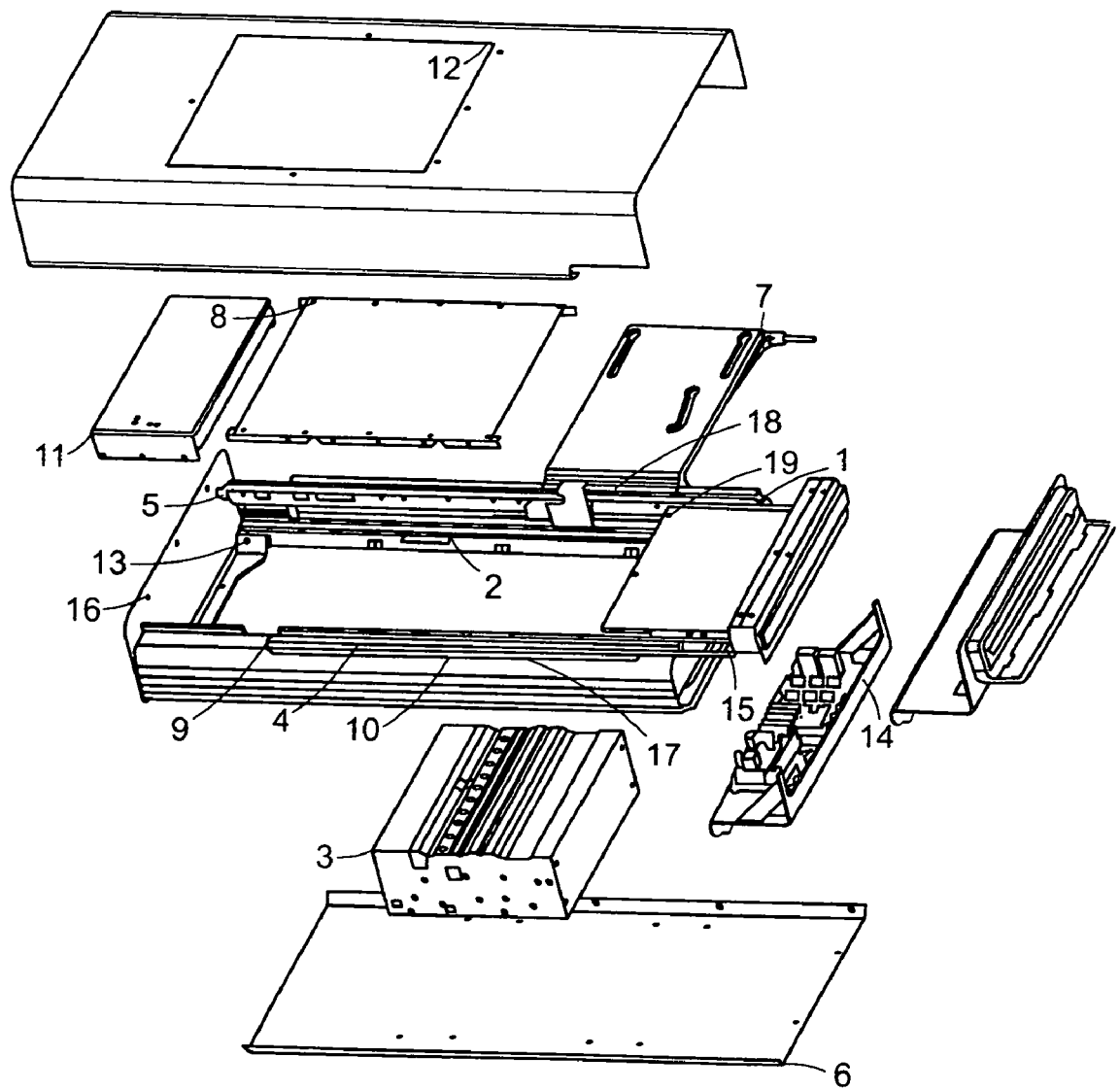
FIG. 13 shows an exploded view of the combination CR DR apparatus of the present invention.
Figure 14A:
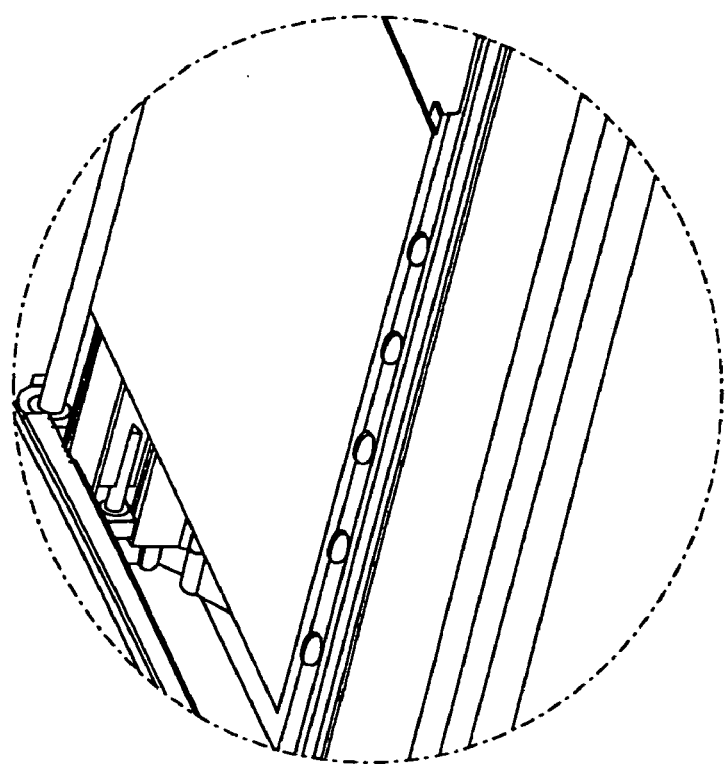
FIG. 14 shows a partial exploded view of an embodiment of the combination CR DR apparatus of the present invention and particularly of the plate positioning assembly allowing the fixed plate to be moved out of the way such that the system may be used in CR mode.
Figure 14:
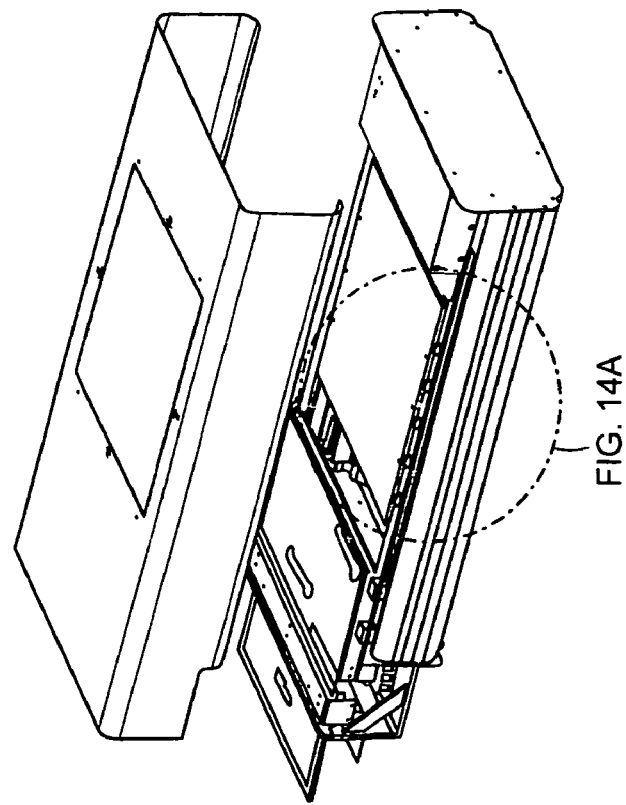

Referring now to FIG. 10, the scanning assembly 102 is shown partially installed or removed from the frame assembly 104. In this embodiment, the scanning assembly 102 is installed or removed by simply uncoupling one or both of the rail supports 119 from frame assembly 104. Rail supports 119 are secured to lateral frame elements 109 and 109 through a plurality of fasteners. The scanning assembly 102, rails 103 and rail supports 109 can then simply be lifted out and removed from within the frame assembly. To fully remove the scan head 102, the electrical couplings between it and the electronics module and electrical interface must also be disconnected. Alternatively, the rail hearing 116 opposing the drive assembly 110 side may be a partial cylinder bearing such that it can be removed and installed on the rail 103 by merely lifting it off the rail. In this way, scanning assembly 102 may be removed and installed by simply removing the two rail supports 119 on the drive side rail 103. Alternative embodiments are contemplated wherein the scanning assembly 102 is secured to the DR device 100 through using any variety of fasteners, clips or other ell known methods. In another embodiment, vibration dampeners are used between the scanning assembly 102 and the frame assembly 104.

Once the scanning assembly module 102 is installed into the frame assembly 104 as generally illustrated in FIG. 8, the drive block and bracket 114 may be connected to the scanning assembly. An electronics module and imaging plate module (not shown) are also installed within the frame assembly 104 in similar fashion to the disclosed CR device embodiment of the present invention. An upper exterior cover 118 as illustrated in FIG. 7 and a lower exterior cover (not shown) are secured to the frame assembly 104 to provide further structural integrity while excluding light, dust and contaminants. Covers 118 are secured to the frame assembly 104 through fasteners though any method of securing typical sheet metal, plastic, composite or similar covers may be used. In the present embodiment, removal of the upper cover 118 allows access to the modular components, such as the scanning assembly 102.

An imaging plate, such as a phosphor plate (not shown) may be secured to a support backing, such as a carbon fiber plate, that is in turn secured to frame assembly 104. The support hacking is preferably transparent to x-rays and may be made from a carbon fiber, a glass or any other x-ray transparent material and may even be a plurality of materials with only the 'read' area being made from x-ray transparent materials. The support backing provides a rigid support for the imaging plate and means for readily securing it to the frame assembly 104. The support backing may be secured to the frame embers 105 and 106 using fasteners and positioned such that the scanning assembly 102 and particularly, the scanning and reading slot 4 of FIG. 1 can be moved over the entire plate.

The imaging plate may be glued or otherwise adhered to backing or may be secured using any other means or methods as commonly known. In one embodiment, a flexible phosphor plate of approximately 14 inches by 17 inches is adhered to an approximately 15 inch by 19 inch by approximately ¼ inch thick carbon fiber backing plate. In another embodiment, a phosphor imaging material, such as a needle or splined phosphor is directly deposited on the x-ray clear backing plate. To enhance durability and prevent contaminants, a protective surface or coating that is also clear to x-rays, such as a carbon fiber plate, may be applied over the needle phosphor material.

Referring now to FIGS. 11-14, an embodiment of the present invention combines both the disclosed CR device of the present invention with the scanning DR device of the present system. In this embodiment, the devices of both systems are used, including the fixed imaging plate as well as the cassette carriage of the CR design. By using a positioning mechanism to move the fixed plate from a position adjacent the elongated scanning slot in the scan head away and to a second position that is away from the scanning assembly, room is made to allow for the cassette carriage assembly to be driven across the scanning assembly. The positioning mechanism is preferably a plurality of rotating mechanical arms that simply swings the fixed imaging plate between two positions.

The frame assembly supports a generally fixed imaging storage plate that is movable between a first position and a second position. In the first position, the fixed imaging plate is retracted away from the scanning path so as to allow sufficient room for the cassette carriage assembly to pass. In this mode of operation, the radiography device acts as a CR system as the scanning assembly acquires images from cassettes loaded into the cassette carriage assembly.

The fixed imaging plate may also be moved into a second position through a series of rotating members and linkages coupling the fixed imaging plate to the frame assembly and moving it relative to the scanning assembly. Prior to moving into the second position, the cassette carriage may be locked to prevent further loading of imaging plates. In the second position, the radiography device operates and functions as a DR system by utilizing the fixed imaging plate within the housing to store and then acquire images. In this mode of operation, the x-ray images are taken over the desired object or patient and the radiography device, which houses the fixed imaging plate. There is no need to remove the imaging plate from the carriage to take new images. In this second position, the fixed imaging plate is advantageously moved from the first retracted position within the exterior housing to the second position adjacent the scanning assembly to allow proper scanning and image acquisition. In yet another embodiment, the imaging plate may be moved into either the first or second position from the cassette carriage assembly.

In another embodiment of the present invention, the radiology device is adapted for scanning larger imaging plates. In this embodiment, the scanning assembly is used in conjunction with a longer frame and drive assembly along with a larger cassette carriage assembly all of which are adapted for use with the longer or even multiple imaging plates such that the scanning head assembly is allowed to continuously or incrementally scan along a longer run, either in the fixed DR mode or the CR mode of operation.

The foregoing description of the embodiments of the invention has been presented for the purposes of illustration and description. It is not intended to be exhaustive or to limit the invention to the precise forms or methods disclosed. Persons skilled in the relevant art can appreciate that many modifications and variations are possible in light of the above teaching.

What is claimed is:

1. A radiography device for use with a fixed imaging plate and an imaging plate cassette, the device comprising:

A frame assembly having a plurality of elongated frame members spaced apart along a parallel axis;

A modular scanning assembly having a housing removeably coupled between the spaced apart elongated frame members, said scanning assembly further comprising an optical assembly and a light collecting assembly and adapted for scanning a focused laser beam across and measuring light energy received from the imaging plate;

A cassette carriage assembly moveably coupled to at least one of the elongated frame members and adapted for receiving and ejecting an imaging plate cassette and for sensing the existence of a cassette; and A drive assembly coupled to the cassette carriage assembly and to at least one elongated frame member, said drive assembly adapted to move the cassette carriage relative to the scanning assembly so that an imaging plate within the cassette carriage may be scanned by the scanning assembly;

A first imaging plate moveably coupled to the frame assembly between a first position adjacent the scanning assembly wherein it can be scanned by the scanning assembly a second position a greater distance from the scanning assembly wherein an imaging plate cassette may be loaded into the cassette carriage and scanned by the scanning assembly; and A plurality of covers coupled to at least one of the elongated frame members so as to enclose a substantial portion of the computed radiography device;

Wherein the device may be converted to a cassette scanning computed radiography device whenever a cassette is sensed within the cassette carriage and the fixed imaging plate is moved to the second position away from the scanning assembly.

2. The radiography device of claim 1 further comprising a plurality of linkage arms for rotating the fixed imaging plate between the first position and the second position.

3. The radiography device of claim 2 further comprising a motor for moving at least one of the linkage arms between the first position and the second position.

4. The radiography device of claim 3 further comprising an electronics module that is electronically connected to the scanning assembly and to the drive assembly, said electronics module adapted for controlling the operations of the scanning assembly and drive assembly so as to acquire imaging data from the scan head assembly.

5. The radiography device of claim 4 wherein the elongated frame members comprises an extrusion from an aluminum alloy.

6. The radiography device of claim 5 wherein each elongated frame member comprises a plurality of elongated frame member mechanically coupled together to form an integral frame member and side member.

7. The radiography device of claim 5 wherein the optical assembly is adapted for generating and scanning a laser beam though a narrow elongated opening along one side of the housing and the light collection assembly further comprises a plurality of reflective surfaces that are adapted to reflect light received from a laser scanned imaging plate to a light measuring device; and wherein at least a portion of the reflective surfaces comprises a synthetic fluoropolymer to enhance reflectivity.

8. The radiography device of claim 2 wherein the scanning assembly further comprises an erasure assembly coupled to the housing and adapted for altering the energy stored in the imaging plate after being scanned.

9. A combination computed radiography and scanning direct radiography device for use with an imaging plate comprising:

A frame assembly having a pair of generally opposing elongated frame members spaced apart along a common axis;

A scanning assembly having an external housing removably coupled between the spaced apart elongated frame members, said scanning assembly further comprising an optics assembly and a light collection assembly mounted within the housing, said optical assembly adapted for generating and scanning a focused laser beam through a narrow elongated opening along one side of the housing and across the imaging plate and said light collection assembly further comprising a plurality of reflective surfaces and adapted to reflect light received from a laser scanned imaging plate;

An imaging plate cassette carnage assembly coupled to the frame members and adapted to receive and eject an imaging plate cassette;

A first imaging plate moveably coupled to the frame assembly between a first position adjacent the scanning assembly wherein the fixed imaging plate can be scanned by the scanning assembly and stored images acquired and a second position a greater distance from the scanning assembly wherein an Imaging plate cassette may be loaded into the cassette carriage and scanned by the scanning assembly; and A positioning mechanism coupled to said frame and said imaging plate and adapted to move said imaging plate between the first position adjacent the elongated opening of the scanning assembly and the second position wherein the scanning assembly may be scanned over a cassette within the cassette carriage assembly;

A guide rail coupled to at least one elongated frame member and adapted for moveably supporting the scanning assembly; and A first drive assembly coupled to the scanning assembly and to at least one elongated frame member, said drive assembly adapted to move the scanning assembly relative to an imaging plate secured within the exterior housing such that the imaging plate may be scanned by the scanning assembly; and A second drive assembly adapted to move the fixed imaging plate between e first position and the second position; and a plurality of covers coupled to at least one of the elongated frame members so as to substantially enclose the radiography device, at least one of said covers adapted to readily allow transmission of x-rays onto the fixed imaging plate.

10. The radiography device of claim 9 further comprising a plurality of linkage arms for rotating the fixed imaging plate between the first position and the second position.

11. The radiography device of claim 10 wherein the second drive comprises a motor for moving at least one of the linkage arms between the first position and the second position.

12. The radiology device of claim 11 wherein the motor comprises an electric motor.

13. The direct radiography device of claim 12 further comprising an electronics module that is electronically connected to the scanning assembly and to the drive assembly, said electronics module adapted for controlling the operations of the scanning assembly and drive assembly so as to acquire imaging data from the scan head assembly.

14. The direct radiology device of claim 13 wherein the fixed imaging plate is a needle phosphor plate.

15. The direct radiology device of claim 13 wherein the phosphor imaging plate is a needle phosphor deposited onto a carbon fiber plate.

* * * * *